US010732269B2

(12) United States Patent
Hope Simpson et al.

(10) Patent No.: US 10,732,269 B2
(45) Date of Patent: Aug. 4, 2020

(54) ULTRASOUND BLOOD FLOW DOPPLER AUDIO WITH PITCH SHIFTING

(71) Applicant: KONINKLIJKE PHILIPS N.V., Eindhoven (NL)

(72) Inventors: David Hope Simpson, Bothell, WA (US); David W. Clark, Derry, NH (US); Anup Agarwal, Millcreek, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 310 days.

(21) Appl. No.: 15/644,135

(22) Filed: Jul. 7, 2017

(65) Prior Publication Data
US 2017/0307742 A1    Oct. 26, 2017

Related U.S. Application Data

(63) Continuation of application No. 13/320,233, filed as application No. PCT/IB2010/051712 on Apr. 19, 2010, now Pat. No. 9,702,969.

(60) Provisional application No. 61/177,673, filed on May 13, 2009.

(51) Int. Cl.
| A61B 8/06 | (2006.01) |
| A61B 8/08 | (2006.01) |
| G01S 7/52 | (2006.01) |
| G01S 15/89 | (2006.01) |

(52) U.S. Cl.
CPC ............ *G01S 7/52066* (2013.01); *A61B 8/06* (2013.01); *A61B 8/488* (2013.01); *G01S 15/8979* (2013.01)

(58) Field of Classification Search
CPC ........ G01S 15/8979; A61B 8/488; A61B 8/06
See application file for complete search history.

(56) References Cited

U.S. PATENT DOCUMENTS

| 4,819,652 A | 4/1989 | Micco |
| 4,868,476 A | 9/1989 | Raspaut |
| 5,641,927 A | 6/1997 | Pawate |
| 6,050,942 A | 4/2000 | Pedersen |
| 6,221,020 B1 | 4/2001 | Lysyansky et al. |
| 6,390,980 B1 | 5/2002 | Peterson |
| 7,666,142 B2 | 2/2010 | Uchibori |
| 2003/0221542 A1 | 12/2003 | Kenmochi |

(Continued)

FOREIGN PATENT DOCUMENTS

| JP | 6061209 U | 8/1994 |
| JP | H0997091 A | 4/1997 |

(Continued)

*Primary Examiner* — Jeffrey G Hoekstra
*Assistant Examiner* — Jason M Ip

(57) ABSTRACT

An ultrasonic diagnostic imaging system produces audio Doppler from detected Doppler signals. The Doppler signals are detected in a band of frequencies which corresponds to the velocity of blood flow signals, and Doppler information is displayed based on the detected band of frequencies. The audio Doppler system produces Doppler audio in a frequency band which is shifted in pitch from the detected band of frequencies. The operator of the ultrasound system is provided with a user control by which the degree of pitch shifting can be controlled. The ultrasound system displays Doppler blood flow velocities referenced to a transmit Doppler frequency $f_0$, with the audio Doppler being shifted in pitch from the frequencies corresponding to the blood flow velocities.

18 Claims, 5 Drawing Sheets

(56) References Cited

U.S. PATENT DOCUMENTS

| | | | |
|---|---|---|---|
| 2007/0167790 | A1 | 7/2007 | Kim et al. |
| 2010/0234731 | A1 | 9/2010 | Lu et al. |

FOREIGN PATENT DOCUMENTS

| | | | |
|---|---|---|---|
| JP | 2002532119 | A | 10/2002 |
| JP | 2008036095 | A | 2/2008 |
| WO | 0034802 | A1 | 6/2000 |
| WO | 20070023438 | A2 | 3/2007 |

ULTRASOUND BLOOD FLOW DOPPLER AUDIO WITH PITCH SHIFTING

CROSS-REFERENCE TO PRIOR APPLICATIONS

This application is a Continuation of application Ser. No. 13/320,233, filed Nov. 11, 2011, which is a U.S. National Phase application under 35 U.S.C. § 371 of International Application No. of PCT/IB2010/051712, filed Apr. 10, 2010, which claims the benefit of U.S. Provisional Patent Application No. 61/177,673, filed on May 13, 2009. These applications are hereby incorporated by reference herein This invention relates to medical diagnostic ultrasound systems and, in particular, to ultrasound systems which produce Doppler audio which can be controlled in pitch.

The use of Doppler audio to diagnose blood flow extends back for many decades. In the years before real time video presentations of Doppler flow characteristics were possible, audio was the only means of ultrasonically diagnosing blood flow. The clinician would aim the Doppler probe toward the organ or vessel of interest, unaided by video, and listen for the characteristic pulsatile "whooshing" sound of blood flow. Since the Doppler frequency shift is generally in the kilohertz range or lower, the amplified Doppler frequency signal could be used to directly drive an audio loudspeaker. This remains the way that ultrasonic Doppler signals from blood flow are produced today. The diagnostic use of audio Doppler has declined, however, as the live video presentations of Doppler flow such as spectral Doppler and colorflow Doppler have provided more precise and spatially specific ways of ultrasonically diagnosing blood flow characteristics. Nevertheless, Doppler audio remains a staple of diagnostic ultrasound and is still used today to help guide and confirm proper probe and sample volume placement. When the visual display viewed by the sonographer and the Doppler audio heard by the sonographer are both producing corresponding information, the sonographer's confidence in the validity and accuracy of the diagnostic information is reinforced.

The Doppler audio signal is played through a sound system which is part of the ultrasound system. In cart-mounted systems the loudspeakers of the sound system can be located at a variety of positions on the cart, such as in the system mainframe, on the control panel, or on the display. Since the loudspeakers are carried by the cart and can be positioned in various places, a wide variety of commercially available loudspeakers are available for use by the system designer. But with the recent advent of more compact, hand-carried ultrasound systems, the space for loudspeakers is much more greatly restricted. In compact systems, size and weight are at a premium and the system designer is often restricted to using very small, very compact loudspeakers. In the CX50 compact ultrasound system of Philips Healthcare, for example, the loudspeakers are mounted in the carrying handle, mandating the use of very small, very thin profile speakers. By their nature, small loudspeakers will generally have a higher range of frequency response than larger speakers, an outcome dictated by both their small size and restricted acoustic environment. These speakers are not capable of the higher fidelity low frequency (bass) response characteristic of larger loudspeakers in larger acoustic enclosures.

As indicated above, the loudspeakers of an ultrasound system must reproduce audio sounds of the Doppler signal frequency range. The frequencies of the Doppler signal are proportional to the speed or velocity of blood flow. For relatively higher velocity blood flow, good fidelity reproduction is generally within the capability of the small speakers of a portable system, as the higher frequency sounds from the higher velocity flow are within the reproducible frequency range of the speakers. These higher blood flow velocities are usually encountered when diagnosing arterial blood flow. But in venous flow diagnosis, the blood flow velocities are much lower. Venous blood flow in the saphenous veins of the leg may be in the range of only a few centimeters per second, for instance, or lower. Consequently the Doppler audio reproduced from these low flow rates will be low frequencies which are poorly reproduced by small speakers. The Doppler audio will be of low volume, garbled, and difficult to comprehend. Hence it would be desirable to provide better audio reproduction of the lower frequencies encountered especially in venous ultrasound exams.

One approach to the problem of low frequency reproduction has been tried for the tissue Doppler mode. In tissue Doppler, the motion of tissue, such as the motion of the myocardium of the heart, is detected by Doppler processing. Unlike blood flow, the motion of tissue is the movement of a continuous section of tissue, in which the tissue cells are moving in unison since they are physically joined together. Thus, the tissue motion will be dominated by the unitary speed of the joined tissue cells and not the range of velocities produced by turbulent blood flow. As a result, the Doppler signal will be characterized by a predominant single frequency at any short interval of time. The mean frequency value is used to generate a synthetic sinusoid at the mean frequency. To reproduce the Doppler signal at a higher frequency it is only necessary to multiply the mean frequency by a frequency scaling term to shift the sinusoid frequency to a higher frequency. A 60 Hz signal can be simply modulated up to 180 Hz, for instance by multiplying the frequency of the synthesized sinusoid by three.

While successful for tissue Doppler, this mean frequency shifting approach is inadequate for Doppler audio of blood flow. As mentioned above, the blood cells in a vein or artery are disassociated and will move in the blood flow substantially independent of each other. The flow velocity at the center of a blood vessels will be greater than the rate along the vessel walls due to friction at the vessel walls which is absent in the center of the vessel. Blood cells can also move in many different directions due to turbulence caused at obstructions and valves. Consequently, blood flow is not characterized by a single velocity as tissue is, but by a multitude of simultaneous velocities. It is the spectrum of audio frequencies corresponding to these velocities which is produced by Doppler audio, which to a trained ear is rich in harmonics and subtle timbre. Trained sonographers rely upon this richness of the Doppler audio sound to guide them in probe and sample volume placement. Simply shifting the mean frequency of the Doppler signal to a higher frequency cannot reproduce the full spectrum of Doppler shift frequencies arising from blood flow and will produce a monotonic, artificial sound that is unfamiliar to the trained sonographer. Consequently a different approach must be taken to the problem of improving the reproduction of low frequency venous flow audio Doppler sounds.

Diagnosis and use of Doppler audio requires considerable experience, as the nuances of the complex Doppler sounds can be very subtle and are contextually comprehended only by trained sonographers. This challenge is made more difficult by the fact that the Doppler demodulation frequency plays a role in the Doppler audio sound. While Doppler harmonic imaging (used primarily for tissue PW Doppler and contrast imaging) uses a demodulation frequency twice that of the transmitted frequency so as to detect the second harmonic of the transmit frequency, conventionally the Doppler demodulation frequency is set equal to the transmit frequency for optimal blood-flow detection in the absence of contrast agents. A probe which transmits and receives at 3 MHz (a 3 MHz probe) will produce a different range of Doppler audio than a 5 MHz probe for instance, and the sonographer will select a different frequency probe for different exams depending upon factors such as the depth of the blood vessel to be examined. It would be desirable if this difference in Doppler frequency bands could be eliminated so that the Doppler audio would be reproduced at the same range of audio frequencies regardless of the frequency of the probe.

In accordance with the principles of the present invention, a diagnostic ultrasound system is described which produces blood flow Doppler audio at an audio frequency which is not the Doppler shift frequency. In one implementation the sonographer is provided with a user control that enables adjustment of the pitch of the Doppler audio signal. The control preferably enables the Doppler audio sound to be shifted in pitch by fractions of an octave or by an octave or more. This is done, not by simply shifting the mean frequency of the Doppler audio band, but by stretching or dilating the entire range of frequencies within the audio band so that the nuances of the blood flow tones are accurately preserved and reproduced. While the sounds of the Doppler audio are shifted in pitch, visual display of the Doppler blood flow velocities is done at the unshifted Doppler velocity frequencies. The user control can cause the Doppler audio signal to be produced at a higher octave during venous flow exams with a small speaker ultrasound system, for instance. In another implementation, pitch control is used to reproduce audio Doppler in a constant frequency spectrum, thereby eliminating the difference in Doppler audio due to the use of different frequency probes.

Figure 1:
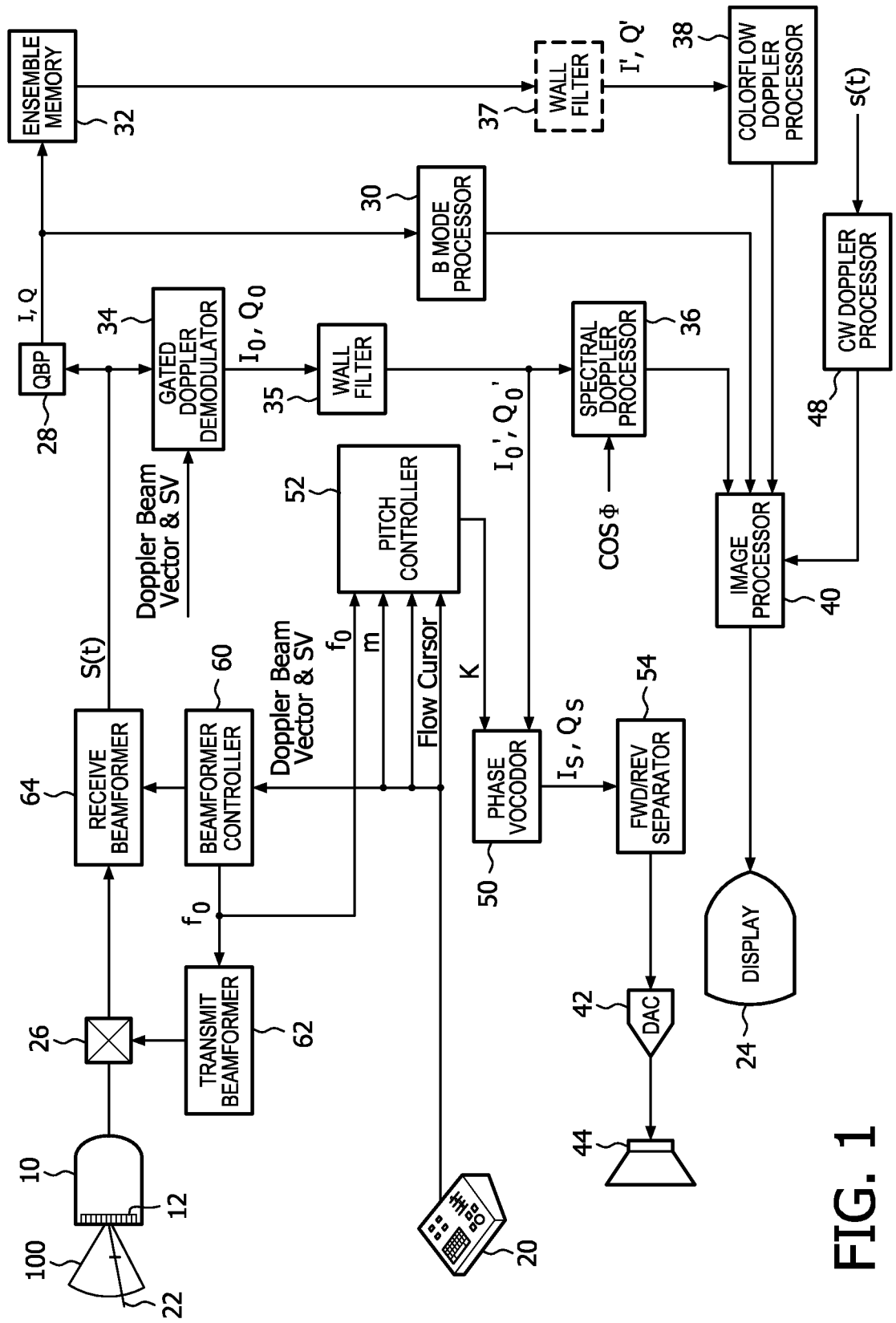
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. The array transducer 12 of an ultrasound probe 10 transmits ultrasonic waves and receives ultrasonic echo signals in response to the transmitted signals. The elements of the array transducer 12 are shown transmitting ultrasound beams over a sector-shaped field of view 100 and along a Doppler beam axis 22. The transmission of ultrasound by the array transducer is controlled by a transmit beamformer 62 which controls parameters such as the frequency of transmission and the timing of transmission by the individual elements of the array. The elements of the transducer array convert the received ultrasound signals to electrical signals which are transmitted by way of a transmit/receive (T/R) switch 26 to a receive beamformer 64. The receive beamformer 64 forms coherent echo signal samples S(t) from the signals received from the transducer elements. The transmit and receive beamformers are synchronized and controlled by a beamformer controller 60.

The coherent echo signals are generally received along a sequence of beam directions and the echo signals undergo quadrature detection by a quadrature bandpass (QBP) filter 28. A typical QBP filter is described in U.S. Pat. No. 6,050,942 (Rust et al.) The QBP filter 28 produces quadrature I and Q components for each echo signal. These components may be amplitude detected to form grayscale image data by a B mode processor 30 using the expression $\sqrt{I^2+Q^2}$. The I,Q component pairs are also stored in an ensemble memory 32 in temporally different samples from the same image field location for Doppler processing. The ensemble memory facilitates a transform from "fast time," which is a function of the r.f. sampling rate, to "slow time," which is a function of the pulse repetition interval (PRI) at which each sample volume in the image field is interrogated. The data ensembles are coupled to a wall filter 37 which removes undesired Doppler shift components. For blood flow imaging the wall filter 37 removes low frequency components from slow-moving tissue, and for tissue motion imaging the higher frequency components of flowing blood are removed. The instantaneous frequencies at different points in the image field may be color-coded in correspondence with the frequencies (which correspond to velocities) and displayed in a color Doppler display by a colorflow Doppler processor 38. The color Doppler display generally overlays a grayscale B mode image for structural orientation of the color-coded motion or flow. The colorflow Doppler display will give the clinician a view of the instantaneous flow or motion over the full image field, dynamically shown in real time.

The ultrasound system of FIG. 1 is also capable of continuous wave (CW) Doppler measurements. In CW Doppler a Doppler signal is transmitted continuously from one aperture of the array transducer 12 and echoes are continuously received by another aperture of the transducer array. The echoes received are those from the overlap of the transmit and receive beams. The received signals s(t) are mixed with sine and cosine functions of the transmit frequency and low pass filtered to remove undesired mixed components, generally the sum frequencies. The difference frequencies are then image processed and displayed spectrally in the same manner as a pulsed wave (PW) spectral Doppler display.

Figure 2:
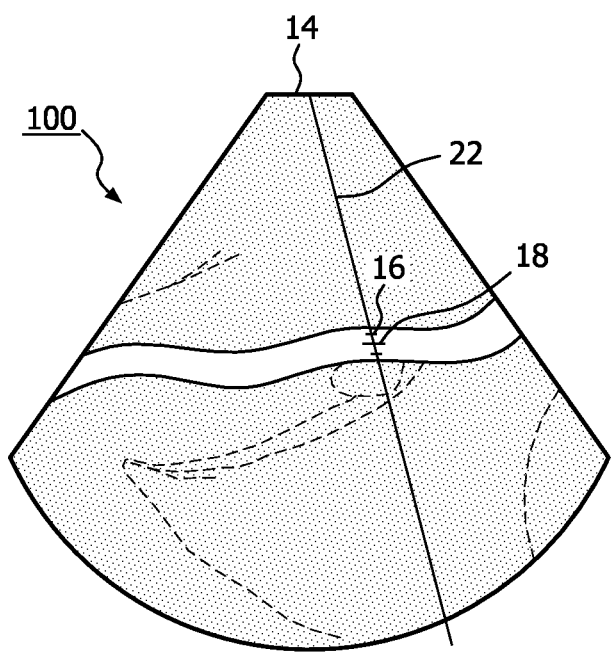
FIG. 2 illustrates an ultrasound system display screen showing a spectral Doppler display and a 2D image of the sample volume and flow cursor locations.
Figure 2:
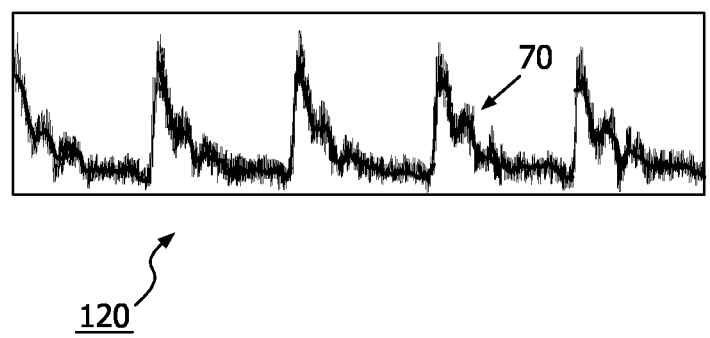

In accordance with the principles of the present invention the received echo signals S(t) are phase demodulated to the Doppler shift band by a gated Doppler demodulator 34. The gating demodulates echoes returned from a sample volume location which may be provided by the Doppler beam vector and sample volume gating signal discussed below. The demodulated Doppler signals $I_0, Q_0$ are referenced to the transmit Doppler frequency $f_0$ and are of the form $I(t)+jQ(t)$, sometimes referred to as the "analytic signal." The demodulated Doppler signals are filtered by a wall filter 35 to remove tissue components and pass only blood flow components. The wall filtered blood flow Doppler signals are of the form $I_0', Q_0'$. These blood flow signals are then processed for spectral display by a spectral Doppler processor 36. For spectral Doppler display the spectral Doppler processor will produce a spectrum of frequency values which correspond to the range of frequencies of blood flow that exist at the time of the measurement. Each time-sequential spectrum is displayed as a spectral line in a (generally scrolling or sweeping) spectral display by the spectral Doppler processor 36 as shown in FIGS. 2 and 3. The spectral Doppler display will give the clinician a detailed quantification of the flow or motion components at a specific sample volume in the image field. The grayscale (B mode) image data, the spectral Doppler data, the CW Doppler data, and the colorflow data are all coupled to an image processor 40 for the production of one or more images in the desired image format(s) on a display 24.

In accordance with the principles of the present invention the ultrasound system of FIG. 1 also produces an audio Doppler signal from a loudspeaker 44. Conventionally the audio Doppler signal is at Doppler-shifted frequencies based on the transmitted Doppler frequency $f_0$ and produced as an audio signal since the Doppler-shifted frequencies are in the human audible spectrum, typically 100 Hz to 10 kHz. When the Doppler audio signal is formed digitally, it is converted to an analog signal by a digital to analog converter (DAC) 42, amplified, and applied to the loudspeaker 44. The audio signals may also be separated as a function of the flow direction with respect to the transducer array by a forward/reverse separator 54, which will reproduce signals from flow toward the transducer array through one speaker and flow away from the transducer array through a second speaker. The flow direction is conveniently given by the sign of the Doppler shift. In addition, the ultrasound system of FIG. 1 enables the user to control the pitch of the audio Doppler signal for better fidelity. For example, the loudspeaker 44 may have poor reproduction fidelity of low frequency Doppler signals from low velocity venous blood flow. In that case, the user would increase the pitch of the reproduced Doppler sounds to a frequency range which is more clearly reproduced by the loudspeaker.

In the example of FIG. 1 the ultrasound system has a control panel 20 by which the user can control a number of the Doppler features of the ultrasound system. It will be appreciated that the control panel can be constructed in hardware or as softkeys on a display screen or a combination of the two. A user control can be manipulated by the user to steer a Doppler beam vector 22 over the image field. The vector 22 is graphically produced as a line over the ultrasound image and is the indicator to the ultrasound system of the direction that the Doppler beam is to be transmitted for spectral Doppler interrogation. The user can also manipulate a control of the control panel to position a sample volume graphic 16 (see FIG. 2) at the depth along the Doppler beam where spectral Doppler data is to be acquired. The Doppler beam vector and the sample volume location are coupled to the beamformer controller 60 to inform the controller of the direction in which the Doppler beam is to be transmitted and the depth along the beam where spectral Doppler measurements are to be made. Gating of the Doppler demodulator 34 may be set by the same timing signals. In addition, the user can manipulate a control of the control panel 20 to indicate the direction of blood flow in a blood vessel with a flow cursor. This cursor setting is used by the ultrasound system to correct the Doppler frequency estimate, as the Doppler equation used to estimate the Doppler frequency is angle-dependent upon the angle between the Doppler beam direction and the direction of the blood flow. The beamformer controller also controls Doppler transmission to be at a nominal Doppler transmit frequency of the transducer array, $f_0$. This information is typically supplied to the ultrasound system by a memory device in the probe when the probe is connected to the ultrasound system as described in U.S. Pat. No. 4,868,476 (Respaut). In Doppler operation the probe 10 will transmit the Doppler beam at this nominal transmit frequency and the Doppler shift or frequency will be offset from this nominal frequency.

In the example of FIG. 1, the nominal Doppler transmit frequency $f_0$, the Doppler beam vector setting, and the flow cursor setting are coupled to a pitch controller 52. In addition the pitch controller receives a pitch parameter m which is set by the user from the control panel. The pitch controller is then able to calculate the angle between the Doppler beam vector and the flow cursor and provide this angle in the form of cos Φ to the spectral Doppler processor 36, which uses this term for angle correction of the Doppler estimates. The pitch controller 52 also uses the data it receives to calculate a pitch scaling factor K for pitch control. The factor K and the Doppler frequency $f_D$ from the Doppler frequency estimator 34 are applied to a phase vocoder 50 for control of the pitch of the Doppler audio signal. Phase vocoders have been used in the past for speech synthesis and music editing. However in the ultrasound system of FIG. 1 the phase vocoder 50 is used for Doppler audio by producing pitch-shifted signal components of the form $I_S, Q_S$, which are used by the forward/reverse separator 54 and the DAC 42 to drive the loudspeaker(s) 44 with a Doppler audio sound different from that which is based on the transmitted Doppler frequency $f_o$.

A conventional Doppler ultrasonic imaging system produces a broadband audio signal whose frequency spectrum is related to the velocities of moving scatterers within a region of interest in the body through the Doppler equation. That is, the intensity of the audio signal at each audio frequency is proportional to the sum of the intensities of the acquired ultrasonic echoes from all scatterers moving at a velocity v, where $f_D$ and v are related through the Doppler equation as:

$$f_D = \frac{2vf_0\cos\phi}{c}$$

where $f_0$ is the ultrasonic demodulation center frequency (conventionally equal to the transmit frequency) Φ is the Doppler angle, the angle between the Doppler beam direction and the direction of blood flow, and c is the speed of sound. Normally, once the Doppler frequency is estimated, the Doppler equation is used to calculate the blood flow velocity. However, in an implementation of the present invention, the frequencies of all components of the Doppler audio signal are scaled such that the intensity of the frequency-scaled audio signal at each audio frequency, $f_{D'}$, is now proportional to the sum of the intensities of the acquired ultrasonic echoes from all scatterers moving at a velocity v, where $f_{D'}$ and v are related through the following equation:

$$f_{D'} = K\frac{2vf_0\cos\phi}{c}$$

where k typically is in the range of 1.0<=k<=4.

In the ultrasound system of FIG. 1, the phase vocoder 50 uses the quadrature Doppler components $I_0', Q_0'$ used for spectral Doppler display and the factor K supplied by the pitch controller 52 to produce a new signal for Doppler audio reproduction in accordance with the equation:

$$f_{D'} = K\frac{2vf_0\cos\phi}{c}$$

The factor K in the equation will shift the pitch of the $f_D$ Doppler frequency band to produce a Doppler audio signal $f_{D'}$ with a different pitch set by the pitch scaling factor K. The pitch scaling factor is set by the user's adjustment of the variable term m, where K=f(m). In a constructed embodiment the term m can be sequenced over a range of values with each discrete value producing a one-third octave shift of the Doppler audio sound. Six values are used so that the Doppler audio sound can be increased in pitch by up to two octaves. Adjustment of the user control for Doppler audio pitch change will not affect the Doppler shift frequency values used for the visual spectral and colorflow Doppler displays, which produce their visual information using the unaltered $f_D$ Doppler frequency.

The pitch controller 52 and the phase vocoder 50 can be used in other implementations to provide other benefits. For instance, as mentioned above, since the Doppler equation contains the term $f_0$, the nominal transmit Doppler frequency, the Doppler sound will depend upon the frequency of the particular probe used for the exam. A 3 MHz probe will produce a lower frequency sound than will a 5 MHz probe. The sonographer may have a discerning ear for 5 MHz Doppler audio, for example, and may want the Doppler sound to be referenced to 5 MHz regardless of the probe or Doppler transmit frequency which is used for the exam. This can be done by having the pitch controller 52 set K equal to:

$$K = \frac{5 \text{ MHz}}{f_0}$$

when the factor K is calculated in this manner, the Doppler equation with the K factor becomes:

$$f_{D'} = \frac{2v(5 \text{ MHz})\cos\phi}{c}$$

The factor K thus causes probe-dependent frequency term $f_0$ to be eliminated and the frequency $f_{D'}$ is always a function of a fixed 5 MHz. Thus, the Doppler audio will always sound like that of a 5 MHz probe. Doppler audio with a consistent pitch is produced for Doppler probes of different Doppler frequencies.

In another implementation the factor K may be calculated by the pitch controller 52 to produce Doppler audio sound which is invariant with changes in the Doppler angle. This may be done by calculating K to be:

$$K = \frac{1}{\cos\phi}$$

When this K factor is used in the Doppler equation the Doppler angle is removed from the calculation of the Doppler audio frequency $f_{D'}$.

It will also be appreciated that the two concepts above could be merged to make the Doppler sound invariant to both changes in the Doppler angle and the frequency of the probe used. Embodiments of the present invention can shift the pitch of the audio Doppler signal, without any alteration of the transmitted ultrasonic frequency or the Doppler demodulation frequency.

A typical Doppler display presented on the display 24 for simultaneous colorflow and spectral Doppler interrogation is shown in FIG. 2. In this display the upper sector image 100 contains the B mode structural display overlaid with color information showing the blood flow. The transducer array is positioned at the apex 14 to acquire the image. The blood flow through the vessel passing through the center of the sector image 100 may continually change from red to blue with the pulsatile change in the blood flow velocity, for example. The user can position a Doppler beam direction line 22 over the image 100 with a user control to intersect the blood vessel at a point where a spectral Doppler measurement is to be made. The sample volume graphic 16 is then moved up and down the line 22 with a user control until it is positioned over the blood vessel where the spectral Doppler measurement is to be made. The tilt of the flow cursor 18 is then adjusted by a user control to indicate the direction of blood flow, and the angle between the Doppler beam line 22 and the flow cursor 18 is the Doppler angle for angle correction. The resultant spectral Doppler display 120 of the blood flow at the sample volume 16 is shown at the bottom of the display screen.

The concept of shifting the pitch of the Doppler audio spectrum may be appreciated by referring to FIGS. 3a-3e which show a sequence of spectral lines of a portion 70 of a spectral Doppler display. Each spectral line of the display such as spectral line 70 is comprises of a sequence of data points along the line. The position of a data point on the line represents a velocity value as indicated by the ±V scale to the left of the spectral lines, and each data point has a magnitude which is a function of the content of the frequency bin which provided that velocity. This spectral information may be represented in both frequency and magnitude by the spectral band 80 drawn to the left of the spectral display in FIG. 3b. As the curve 80 illustrating the envelope of the spectral band indicates, the spectrum has a particular shape determined by the range of velocities of blood cells and by the presence of predominate velocities which are represented by increased amplitude of the curve (to the left in the drawings).

Figure 3A:
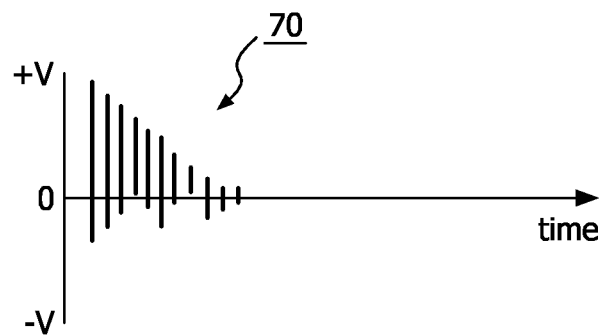
FIGS. 3a-3e illustrate the shifting of the Doppler audio spectrum in accordance with the principles of the present invention.
Figure 3B:
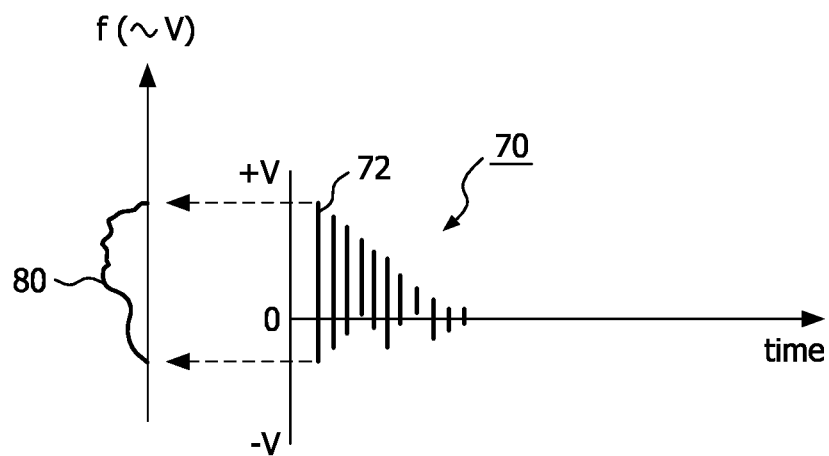
Figure 3C:
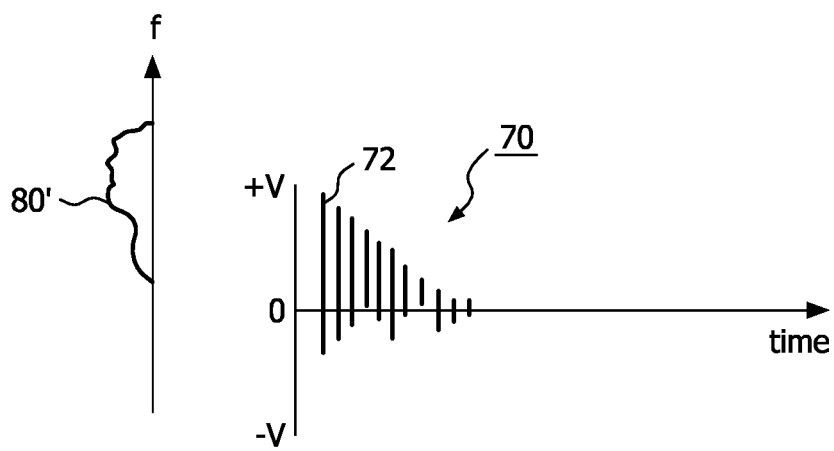
Figure 3D:
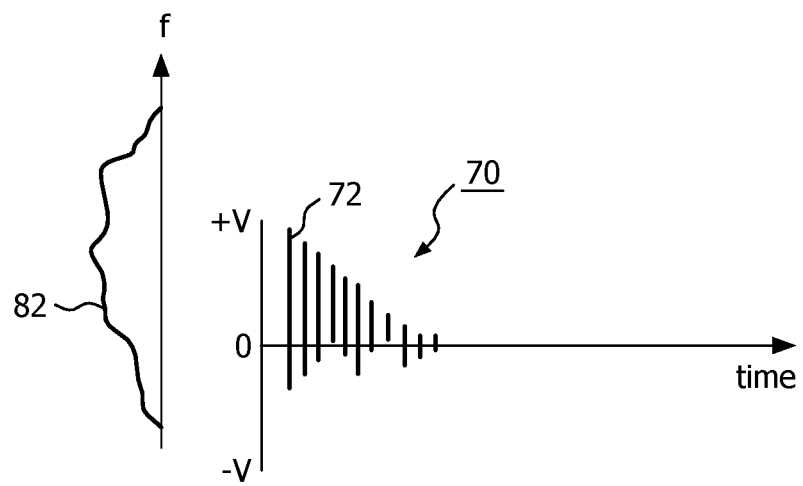
Figure 3E:
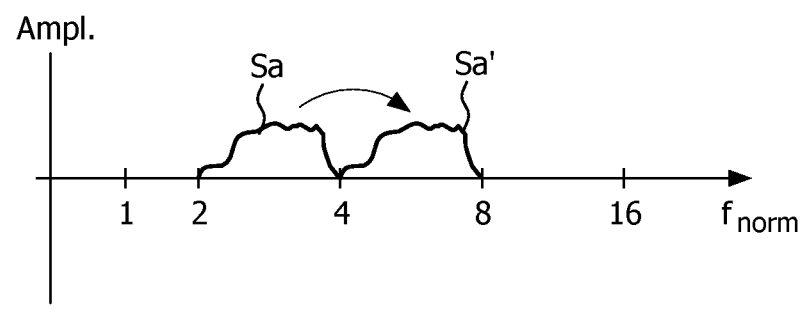

A simple way to change the Doppler sound for a higher frequency response loudspeaker is simply to shift the frequency of the spectrum 80 to a higher frequency band 80' as shown in FIG. 3c. The sound will now be reproduced at the higher frequencies of the shifted band 80'. But this simple frequency shift will not reproduce the timbre of the sound. The higher frequency sound will be metallic and inharmonic and will sound dissonant to the ear of the trained sonographer. To prevent this an implementation of the present invention will shift the pitch of the sound, changing the spectrum 80 of FIG. 3b to the pitch-shifted spectrum 82 of FIG. 3d. In this new spectrum the frequency components have been stretched or dilated, and harmonic relationships retained. It is seen that the shape of the spectral envelope is preserved but stretched. Thus, a 100 Hz component is scaled to 200 Hz, a 200 Hz component is scaled to 400 Hz, a 300 Hz component is scaled to 600 Hz, and so on, which preserves the harmonic content and the timbre of the sound. This effect is shown in a normalized logarithmic frequency scale in FIG. 3e, where the conventional audio spectrum Sa is shifted by one octave to a pitch-shifted spectrum Sa'. It is seen that the spectrum appears unaltered in shape, but is shifted up in pitch by one octave. The pitch-shifted Doppler audio will appear to the sonographer to be the same Doppler sound as before, but at a higher pitch. And when the higher pitch is better aligned with the passband of the loudspeaker, a clearer and more distinct Doppler audio sound is produced by the ultrasound system.

There are a number of techniques for shifting the pitch of the Doppler audio signal such as time domain harmonic scaling, wavelet processing, and use of a phase vocoder. The phase vocoder approach is preferred as phase vocoders are well understood in other applications and a phase vocoder can be implemented with overlapping short-time FFT processing, which is a common approach for Doppler spectral signal processing. The phase vocoder, which can be implemented in hardware or algorithmically by software processing, models the audio signal as a set of narrowband tones, one for each FFT frequency bin. The change of magnitude of an FFT bin between successive overlapping FFTs is interpreted as a gradual change of amplitude of the narrowband tone over that short span of time. The change of phase of an FFT bin between successive overlapping FFTs is interpreted as a precise frequency adjustment of the narrowband tone over that short span of time, a perturbation from the center frequency of the FFT bin. Each frequency-adjusted tone is then used to interpolate the corresponding FFT bin in time with intermediate magnitude and phase values, producing more overlapping FFTs for the same original time span. These overlapping values are processed by inverse-FFT processing and overlapped-added (with the original overlap factor) in the usual way of short-time FFT reconstruction, producing more samples than in the original sampled signal. If replayed at the original sample rate, this would produce time-stretched audio at the original pitch. But if replayed at a faster sample rate to match the original time span, the pitch is scaled up by the FFT interpolation factor. The pitch or time can be scaled down by decimating instead of interpolating the FFTs.

Figure 4:
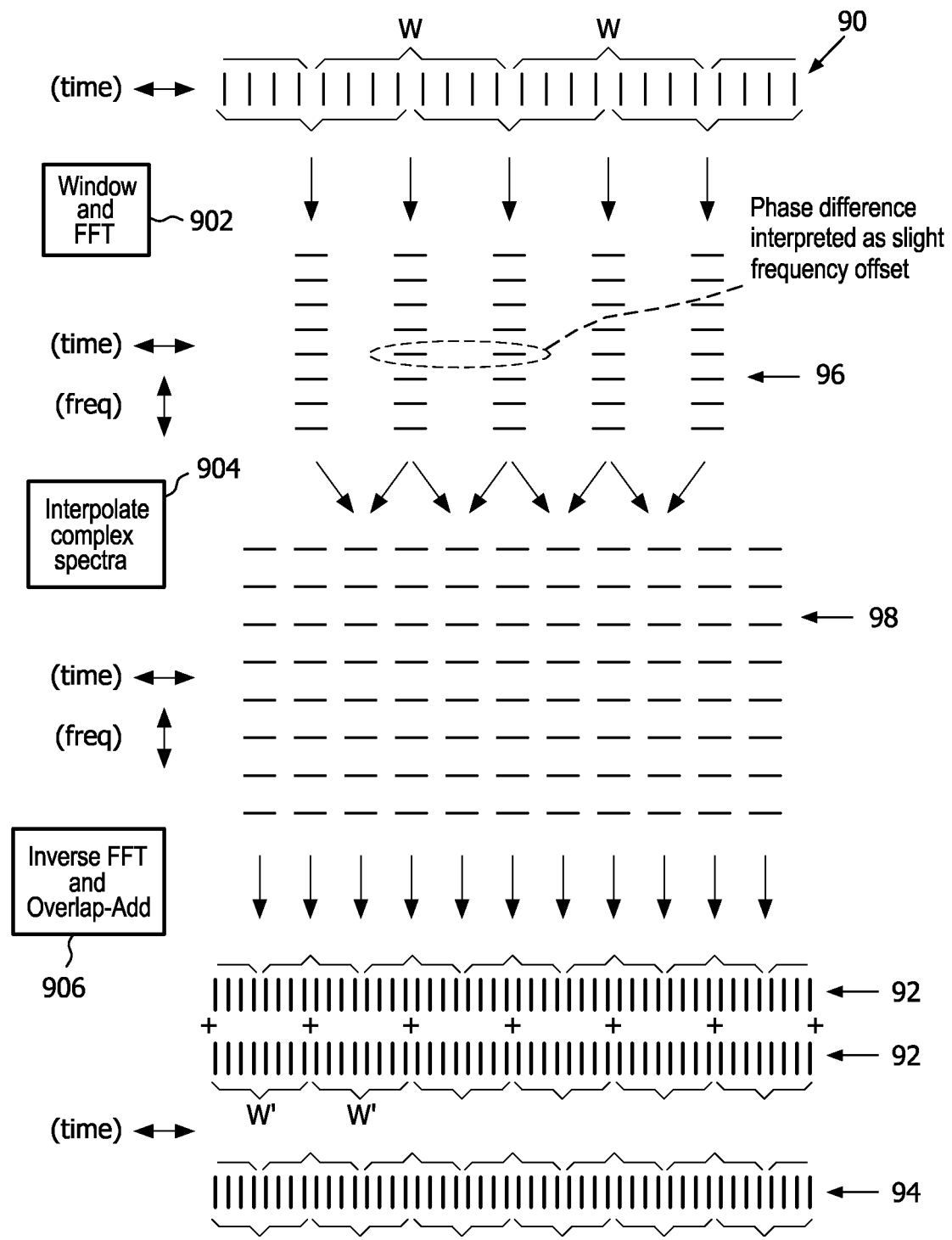
FIG. 4 illustrates a technique for shifting the pitch of a blood flow Doppler audio which may be implemented in a sampled data system.

Phase vocoder processing is illustrated by FIG. 4 as one possible implementation of pitch shifting. In this example the frequencies will be doubled, shifting the pitch up one octave. The small vertical lines 90 represent a sequence of Doppler audio samples before pitch shifting, with time progressing in the horizontal direction and the spacing between the samples representing the sample rate. The sequence of samples can be segmented in overlapping windows W as shown by the brackets above and below the sequence of samples 90. In this illustration each window contains eight samples and is 50% overlapped with adjacent windows, although windows with greater or fewer samples and more or less overlap can be used.

Each segmented window of time samples is multiplied by a smoothly tapered window function, then converted to frequency domain with an FFT (Fast Fourier Transform) in step 902. The smoothly tapered window function is not shown in the figure, but is a standard step in FFT processing to reduce time discontinuity and frequency smearing caused by the FFT treating the time segment as a periodic function. The result of the FFT of successive windows is a time sequence of frequency domain complex spectra, represented by the vertical sets of small horizontal lines 96 in the figure. Each sample (called a "bin") of each spectrum is a complex number, whose magnitude and phase correspond to a windowed sinusoid at the center frequency of the bin. Considering the same frequency bin in two successive complex spectra, the difference in phase over that increment of time can be interpreted as a slight frequency offset from the center frequency of a bin, since frequency is the time derivative of phase. In other words, the center frequency (phase rate) of the bin produces a deterministic large change of phase over the time interval between spectra, and the actual phase difference between the spectra is used as a slight adjustment to this phase rate. Phase calculations are modulo $2\pi$ radians (360 degrees).

Using the slightly adjusted frequencies and the magnitudes for each bin in successive spectra, additional complex spectra 98 are interpolated as shown in the figure and indicated by step 904. In this example, the number of spectra over a span of time is doubled, corresponding to an audio frequency scaling of two, which is a one octave increase in pitch. The complex spectra are then converted back to the time domain with an inverse FFT, producing segmented windows W' of time samples 92, which are added together with the same overlap fraction (50% in this example) as in the earlier window and FFT processing step 902. This is illustrated in the figure with the small vertical lines 92 and brackets W'. Since the interpolation between spectra produced more spectra per unit of time, after the inverse FFT and overlap add there are more samples per unit of time. The frequency content of the data is equivalent to the original audio signal in terms of samples, but the sample rate now higher (doubled in this example). So when the data are converted to a continuous analog signal with the new sample rate and applied to a loudspeaker, all of the frequencies are scaled by the ratio of new to original sample rates.

The frequency scale factor is not constrained to an integer, because the complex spectra can be resampled to any rate. For the time samples to align in the overlap-add step 906 following the inverse FFT, the scaling factor should be a ratio of integers, where the denominator is the number of samples in the window. However, even this constraint can be easily overcome by multiplying each interpolated frequency spectrum with a linear phase ramp corresponding to its fractional sample time shift. So there is essentially no constraint on the quantization of frequency scale factor.

The primary trade-off in the phase vocoder processing is the FFT size. Many small FFTs can better follow temporal transients, but only have a few frequency bins, which can be audible as distinct tones. Few large FFTs can better estimate a continuous frequency spectrum, but have a slow temporal evolution that can be audible as phase smearing. The artifacts become more noticeable or objectionable as the pitch scale factor increases. Thus, the preferred embodiment uses medium FFT sizes corresponding to about 20-30 msec.

If the sample sequence 94 of FIG. 4 were played at the original sample rate of FIG. 4 through the DAC 42 and loudspeaker 44, the audio signal would be a time-stretched version of the audio signal of the sequence 90 of FIG. 4 at the same pitch as the FIG. 4 sequence. But when the sequence 94 is played at a higher sample rate so that each window at the bottom of FIG. 4 is played in the same time interval as a window at the top of FIG. 4, the pitch is scaled up. In the illustrated example where the number of samples in each window is doubled, each window of samples in FIG. 4 is then played at twice the sample rate of FIG. 4 and the pitch is scaled up by a full octave. If the FFT processing is used to decimate the sample sequence instead of upsampling it, the pitch would be scaled down instead of up.

It is seen in FIG. 4 that there is a ratio of the number of samples 90 in the windows W of the original sequence to the number of samples 94 in the windows of the final sequence at the bottom of FIG. 4. This ratio can be expressed as a ratio of integers. In this example the ratio is 8:16 or 1:2. The user control of the control panel which adjusts the pitch of the Doppler audio can provide one of these integers, m.

What is claimed is:

1. An ultrasonic diagnostic imaging system which produces a Doppler audio signal of measured blood flow, the system comprising:
- an ultrasound probe, operating at an ultrasonic Doppler transmit frequency $f_0$, configured to acquire Doppler ultrasound signals in a range of frequencies in a Doppler audio band, said ultrasound signals being referenced to the Doppler transmit frequency from a location of blood flow;
- a Doppler demodulator, responsive to the Doppler ultrasound signals, configured to produce Doppler shift signals of the velocity of blood flow in an audio frequency band;
- a Doppler information display, responsive to the Doppler shift signals, configured to display measured blood flow velocity based upon the Doppler shift signals; and
- an audio Doppler system, responsive to the Doppler shift signals, configured to produce pitch-shifted audio Doppler without changing the displayed blood flow velocity,
- wherein the audio Doppler system is responsive to a user control to shift the pitch of the Doppler-shifted signals by a fractional or integer number of octaves by stretching or dilating the entire range of frequencies within the Doppler audio band and retaining harmonic relationships in the Doppler audio band so as to preserve the timbre of audio Doppler sounds,
- wherein the audio Doppler system is responsive to the user control to produce audio Doppler sounds invariant to changes of a Doppler angle or based on an indication of a direction of blood flow adjusted by a user.

2. The ultrasonic diagnostic imaging system of claim 1, wherein the audio Doppler system is operative to produce pitch-shifted audio Doppler without change in the ultrasonic transmit frequency $f_0$ or the displayed blood flow velocity.

3. The ultrasonic diagnostic imaging system of claim 2, wherein the user control is operable to control a scaling of the frequency band for audio Doppler.

4. The ultrasonic diagnostic imaging system of claim 2, wherein the audio Doppler system further comprises a phase vocoder which shifts the pitch of the Doppler-shifted signals.

5. The ultrasonic diagnostic imaging system of claim 2, wherein the audio Doppler system further comprises a pitch controller, responsive to the user control, which produces a pitch shift factor K for control of the audio pitch shift.

6. The ultrasonic diagnostic imaging system of claim 1, wherein the audio Doppler system further comprises a loudspeaker exhibiting a given frequency response; and wherein the shift in pitch is determined by the frequency response of the loudspeaker.

7. The ultrasonic diagnostic imaging system of claim 1, wherein the Doppler demodulator is operative to produce demodulated Doppler signals in a band exhibiting a demodulation reference frequency, which band is determined by a Doppler equation, wherein the pitch-shifted audio Doppler band is different from the band determined by the Doppler equation and the demodulation reference frequency.

8. The ultrasonic diagnostic imaging system of claim 7, wherein the Doppler equation is of the form $$f_D = \frac{2vf_0\cos\emptyset}{c}.$$

9. The ultrasonic diagnostic imaging system of claim 1, wherein the imaging system is operable with a selected one of a plurality of ultrasound probes, each exhibiting a different nominal Doppler frequency $f_0$.

10. The ultrasonic diagnostic imaging system of claim 9, wherein the Doppler demodulator is operable to detect Doppler signals by a Doppler equation which is a function of $f_0$ of a selected probe; and wherein the audio Doppler system produces audio Doppler related to a selected $f_0$ frequency for probes of different nominal Doppler frequencies.

11. A method of producing a Doppler audio signal of measured blood flow, the method comprising:
- using an ultrasound probe, operating at an ultrasonic Doppler transmit frequency $f_0$, acquiring Doppler ultrasound signals in a range of frequencies in a Doppler audio band, said ultrasound signals being referenced to the Doppler transmit frequency from a location of blood flow;
- based at least partially on the Doppler ultrasound signals, producing Doppler shift signals of the velocity of blood flow in an audio frequency band;
- displaying measured blood flow velocity based at least partially upon the Doppler shift signals;
- producing pitch-shifted audio Doppler without changing the displayed blood flow velocity; and
- in response to a user control, shifting the pitch of the Doppler-shifted signals by a fractional or integer number of octaves by stretching or dilating the entire range of frequencies within the Doppler audio band and retaining harmonic relationships in the Doppler audio band so as to preserve the timbre of audio Doppler sounds,
- wherein in response to the user control, the audio Doppler sounds are produced invariant to changes of a Doppler angle or based on an indication of a direction of blood flow adjusted by a user.

12. The method of claim 11, wherein the producing further comprising producing pitch-shifted audio Doppler without change in the ultrasonic transmit frequency of the ultrasound probe.

13. The method of claim 12, further comprising scaling of the frequency band for audio Doppler in response to the user control.

14. The method of claim 12, wherein shifting the pitch of the Doppler-shifted signals is performed with a phase vocoder.

15. The method of claim 12, further comprising producing a pitch shift factor K for control of the audio pitch shift.

16. The method of claim 11, further comprising determining the shift in pitch based at least partially on a frequency response of a loudspeaker on an ultrasound system.

17. The method of claim 11, further comprising producing demodulated Doppler signals in a band exhibiting a demodulation reference frequency, wherein the band is determined by a Doppler equation, and wherein the pitch-shifted audio Doppler band is different from the band determined by the Doppler equation and the demodulation reference frequency.

18. The method of claim 17, wherein the Doppler equation is of the form $$f_D = \frac{2vf_0\cos\emptyset}{c}.$$

* * * * *